(12) United States Patent
Kawamura et al.

(10) Patent No.: US 11,872,338 B2
(45) Date of Patent: Jan. 16, 2024

(54) AIR TRAP CHAMBER AND EXTRACORPOREAL CIRCULATION CIRCUIT

(71) Applicant: NIKKISO CO., LTD., Tokyo (JP)

(72) Inventors: Shunsuke Kawamura, Makinohara (JP); Ryo Kato, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 660 days.

(21) Appl. No.: 17/049,937

(22) PCT Filed: Mar. 11, 2019

(86) PCT No.: PCT/JP2019/009668
§ 371 (c)(1),
(2) Date: Oct. 22, 2020

(87) PCT Pub. No.: WO2019/211945
PCT Pub. Date: Nov. 7, 2019

(65) Prior Publication Data
US 2021/0236708 A1    Aug. 5, 2021

(30) Foreign Application Priority Data

May 2, 2018    (JP) .................. 2018-088659

(51) Int. Cl.
*A61M 1/36* (2006.01)
*A61M 1/16* (2006.01)

(52) U.S. Cl.
CPC ......... *A61M 1/3638* (2014.02); *A61M 1/1658* (2013.01); *A61M 1/3627* (2013.01); *A61M 2205/3334* (2013.01)

(58) Field of Classification Search
CPC ........... A61M 1/38; A61M 1/32; A61M 5/36; A61M 5/38; A61M 1/14; A61M 1/36;
(Continued)

(56) References Cited

U.S. PATENT DOCUMENTS

| | | | |
|---|---|---|---|
| 4,919,802 A | 4/1990 | Katsura | |
| 6,176,904 B1 * | 1/2001 | Gupta | B01D 36/001 96/219 |

(Continued)

FOREIGN PATENT DOCUMENTS

| | | |
|---|---|---|
| JP | H03-062111 B2 | 9/1991 |
| JP | 3105777 U | 11/2004 |
| WO | 2017/219311 A1 | 12/2017 |

OTHER PUBLICATIONS

English language machine translation of JP310577U, 7 pages, No Date.*

(Continued)

*Primary Examiner* — Pranav N Patel
(74) *Attorney, Agent, or Firm* — Oliff PLC

(57) ABSTRACT

The introduction pipe is extend from an inlet port to the inside of the chamber body, and has, as an end opening thereof, a discharge port provided in the inner circumferential surface of the chamber body so as to be directed toward the circumferential direction. The inner circumferential surface of the chamber body is provided so as to spirally extend, along the circumferential direction, from a discharge point at which the discharge port is disposed, to a connection point at which the outer circumferential surface of the introduction pipe is connected to the inner circumferential surface of the chamber body. The inner circumferential surface is formed such that a second radius connecting the connection point to the center axis of the chamber body is shorter than a first radius connecting the discharge point to the center axis of the chamber body.

4 Claims, 14 Drawing Sheets

(58) Field of Classification Search
CPC ........ A61M 1/3638; A61M 2205/3334; A61M 2205/7545; A61M 2206/16; A61M 1/3627; B01D 19/00; B01D 36/00; B01D 45/12
See application file for complete search history.

(56) References Cited

U.S. PATENT DOCUMENTS

2006/0173395 A1    8/2006  Brugger et al.
2009/0137941 A1*  5/2009  Lynch .................. A61M 1/363
                                                    604/6.11

OTHER PUBLICATIONS

May 21, 2019 Office Action issued in Japanese Patent Application No. 2018-088659.
May 28, 2019 International Search Report issued in International Patent Application No. PCT/JP2019/009668.
Jan. 27, 2022 Extended European Search Report issued in European Patent Application No. 19796241.8.
Dec. 1, 2022 Office Action issued in Chinese Patent Application No. 201980028243.7.

* cited by examiner

AIR TRAP CHAMBER AND EXTRACORPOREAL CIRCULATION CIRCUIT

TECHNICAL FIELD

The present invention relates to an air trap chamber and an extracorporeal circulation circuit including the air trap chamber.

BACKGROUND

For instance, in hemodialysis, blood removed from a patient is sent to an extracorporeal circulation circuit. The extracorporeal circulation circuit includes an arterial side circuit to which the removed blood is supplied, a purifier (dialyzer) that purifies the blood sent from the arterial side circuit, and a venous side circuit that returns the purified blood to the patient. At least one of the arterial side circuit and the venous side circuit is provided with an air trap chamber for capturing bubbles in blood flowing through the circuit (debubbling).

The air trap chamber has an inlet on the upstream side coupled to an arterial side circuit, and an outlet at the downstream side coupled to the venous side circuit. An air vent is also provided at the upstream side. For instance, an inlet and an air vent are provided on a top wall provided at the upper end of the air trap chamber.

For instance, in Patent Document 1, an inlet pipe passing from the inlet through the top wall and extending into the chamber is provided. An ejection port is provided at the lower end of the inlet pipe. Since the ejection port is provided below the top wall, bubbles retained on the top wall are prevented from flowing into the ejection port.

The ejection port is provided at the inner circumference surface of the chamber and is faced in the circumferential direction. With such positioning and orientation, the flow of a liquid (for example, blood or saline solution) ejected from the ejection port becomes a swirl flow that flows along the inner circumference surface of the chamber. Generating a swirl flow in the chamber provides the advantage that the retention in the chamber is less likely to occur than in the case where the liquid is simply dropped into the chamber.

CITATION LIST

Patent Literature

Patent Document 1: US 2006/0173395 A1

SUMMARY

Technical Problem

A possible way to reduce the so-called dead space (dead volume) in the air trap chamber is to locate the liquid level in the chamber as close as possible to the inner surface of the top wall. In this case, the ejection port provided below the top wall is submerged below the liquid level. When the liquid is ejected from the ejection port in this state, as illustrated in FIG. 14, the swirl flow goes into the back (to the backside in the circumferential direction) of an ejection port 102 of an inlet pipe 100 and hits a pipe wall 104, which may diminish the force of the liquid flow and cause retention.

It is therefore an object of the present invention to provide an air trap chamber in which, when the liquid level is set above the ejection port, the flow of a liquid along the inner circumference surface of a chamber can be made smoother than in hitherto-used techniques.

Solution to Problem

The present invention relates to an air trap chamber. The air trap chamber includes a chamber body and an inlet pipe. The chamber body has a substantially cylindrical shape and has an upstream end defined with respect to a central axis and covered with a top wall having an inlet, and a downstream end defined with respect to the central axis and having an outlet. The inlet pipe that extends from the inlet into the chamber body, and has an ejection port, being an end opening, is provided at the inner circumference surface of the chamber body and faced in a circumferential direction. The inner circumference surface of the chamber body extends, in a spiral shape in the circumferential direction, from an ejection point where the ejection port is located to a connection point where the outer circumferential surface of the inlet pipe surrounding the ejection port is coupled to the inner circumference surface of the chamber body. Moreover, a first distance connecting the ejection point and the central axis of the chamber body on a plane perpendicular to the central axis of the chamber body is longer than a second distance connecting the connection point and the central axis of the chamber body on the plane.

According to the aforementioned invention, the distance between the connection point on the back side of the ejection port and the central axis of the chamber body is made shorter than the distance between the ejection point and the central axis of the chamber body, making it possible to reduce the flow rate of the liquid flowing toward the connection point. Hence, the retention of the liquid around the connection point can be suppressed more than in hitherto-used techniques.

In the aforementioned invention, a connection point angle that is formed between a tangent line of the outer circumferential surface of the inlet pipe and a tangent line of the inner circumference surface of the chamber body at the connection point and straddles the outer circumferential surface of the inlet pipe may be 90° or less.

When the connection point angle is an obtuse angle exceeding 90°, the outer circumferential surface of the inlet pipe and the inner circumference surface of the chamber body that define the connection point form a dead-end structure around the connection point, and the liquid that has entered it is likely to be retained. According to the aforementioned invention, avoiding the dead-end structure can prevent retention of the liquid around the connection point.

In the aforementioned invention, an R portion may be formed around the connection point.

With the R portion, the liquid can smoothly move from the inner circumference surface of the chamber body to the outer circumferential surface of the inlet pipe.

In the aforementioned invention, the air trap chamber may have a cap provided on the upstream side and a housing provided on the downstream side. In this case, the cap includes a substantially cylindrical cap body, the inlet pipe in which the ejection port is provided at the inner circumference surface of the cap body and faced in the circumferential direction, and a first connection flange that is connected to the downstream end of the cap body and has a larger diameter than the cap body. The housing includes a second connection flange to be inserted into the first connection flange, and a housing body coupled to the downstream side of the second connection flange. The inner diameter of the second connection flange of the housing is larger than the second distance of the inner circumference surface of the cap body. An R portion or a chamfered portion is formed in at least a portion of the second distance of the downstream end of the cap body.

Although a step extending in the central axis direction is formed based on the inner diameter difference between the downstream end of the cap body and the second connection flange, forming an R portion at this step allows a liquid to move smoothly from the downstream end of the cap body to the second connection flange.

The present invention also relates to an extracorporeal circulation circuit. The removed blood is circulated in the circuit. The air trap chamber according to the aforementioned invention is coupled to the flow path of the extracorporeal circulation circuit.

Advantageous Effects of Invention

According to the present invention, when the liquid level is set above the ejection port, the flow of a liquid along the inner circumference surface of a chamber can be made smoother than in hitherto-used techniques.

DESCRIPTION OF EMBODIMENTS

Figure 1:
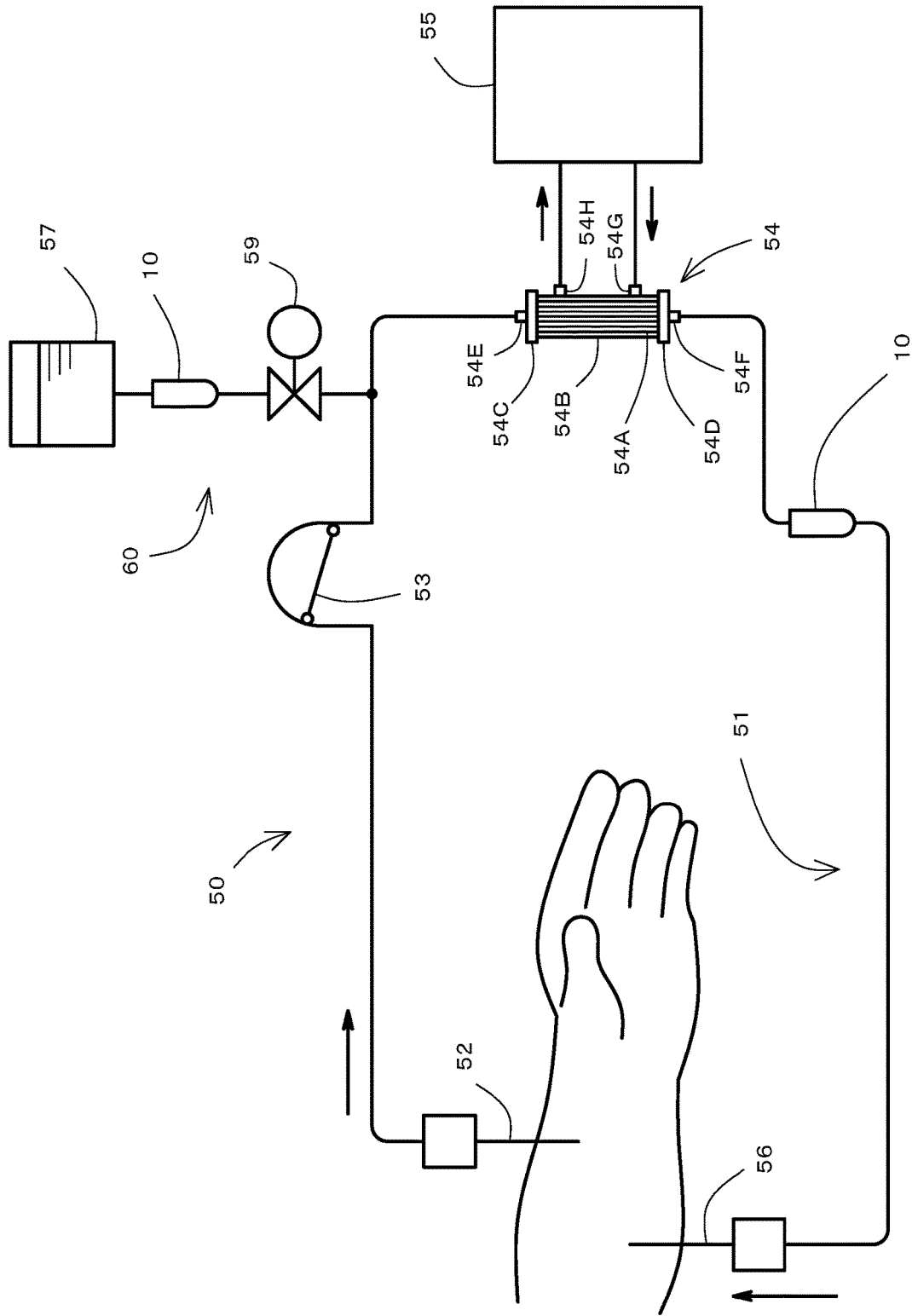
FIG. 1 is a diagram illustrating an extracorporeal circulation circuit using an air trap chamber according to an embodiment.

FIG. 1 illustrates an extracorporeal circulation circuit to which an air trap chamber 10 according to an embodiment is coupled. The extracorporeal circulation circuit is a circuit used for hemodialysis, for example, and includes an arterial side circuit 50, a blood purifier 54, a dialyzer 55, a venous side circuit 51, and a replacement liquid line 60.

Note that the air trap chamber 10 according to the embodiment is coupled to the extracorporeal circulation circuit used for dialysis treatment, but this is not necessarily the case. For instance, the air trap chamber 10 according to the embodiment may be coupled to an extracorporeal circulation circuit that circulates blood removed from a patient and can perform purification treatment. For instance, the air trap chamber 10 according to the embodiment may be coupled to an extracorporeal circulation circuit used in acetate free biofiltration (AFBF), continuous slow hemofiltration therapy, hemadsorption therapy, selective blood cell depletion therapy, simple plasma exchange therapy, double membrane filtration plasma exchange therapy, plasma adsorption therapy, or the like.

The air trap chamber 10 according to the embodiment can be provided in the arterial side circuit 50, the venous side circuit 51, and the replacement liquid line 60, which will be described later, of the extracorporeal circulation circuit. In addition, the air trap chamber 10 according to the embodiment can be coupled to a path where thrombus may occur; that is, an extracorporeal circulation circuit path in which blood or blood components flow. In addition, the air trap chamber 10 according to the embodiment can be coupled to extracorporeal circulation circuit paths in which blood or blood components flow, extracorporeal circulation circuit paths in which saline solution flows, and extracorporeal circulation circuit paths including these.

Referring to FIG. 1, the arterial side circuit 50 is supplied with blood removed from the patient's body. The arterial side circuit 50 includes an arterial side puncture needle 52 and a roller pump 53 from the upstream side. The arterial side puncture needle 52 is introduced into a blood vessel of the patient and the blood is sent to the tube of the arterial side circuit 50 (blood removal).

The roller pump 53 transports the blood in the tube to the blood purifier 54 by externally squeezing the tube. For instance, since the circuit may be filled with a priming liquid from the venous side circuit during priming, the roller pump 53 may be capable of rotating in the forward and reverse directions.

The air trap chamber 10 according to this embodiment may be coupled between the arterial side puncture needle 52 and the roller pump 53 and between the roller pump 53 and the blood purifier 54. The structure and function of the air trap chamber 10 will be described later. It should be noted that the air trap chamber 10 in the venous side circuit 51 is indispensable to make sure to debubble the blood to be returned, whereas these air trap chambers 10 provided in the arterial side circuit 50 are optional.

The replacement liquid line 60 is provided between the roller pump 53 and the blood purifier 54 in the arterial side circuit 50. The replacement liquid line 60 is provided with a replacement liquid bag 57 and a clamp 59. The air trap chamber 10 is provided between the replacement liquid bag 57 and the clamp 59.

The replacement liquid bag 57 contains saline solution as a replacement liquid. For instance, during priming of the extracorporeal circulation circuit, the clamp 59 is opened and the saline solution is supplied from the replacement liquid bag 57 to the extracorporeal circulation circuit. Bubbles in the circuit are removed by filling the circuit with saline solution. Upon completion of the priming, the clamp 59 is closed.

Upon completion of the dialysis treatment, the clamp 59 is opened again to return the blood from the circuit to the patient's body, filling the circuit with saline solution from the replacement liquid bag 57. In other words, the blood in the circuit is replaced with saline solution.

The blood purifier 54 purifies the blood sent from the arterial side circuit 50. The blood purifier 54 is a so-called dialyzer, and the dialysate and blood are exchanged through a hollow fiber membrane 54A, for example. In the blood purifier 54, a bundle of hollow fiber membranes 54A (hollow fiber membrane bundle) is contained in a column 54B.

The column 54B is a cylindrical container member, and has an inlet side cap 54C at one end with respect to the direction of the central axis and an outlet side cap 54D at the other end. The inlet side cap 54C is provided with a blood inlet port 54E coupled to a connector (not shown in the drawing) at the downstream end of the arterial side circuit 50. The outlet side cap 54D is provided with a blood outlet port 54F coupled to a connector (not shown in the drawing) at the upstream end of the venous side circuit 51. Blood sent from the arterial side circuit 50 flows from the blood inlet port 54E into the hollow fiber membranes 54A.

A dialysate inlet port 54G is provided in a portion of the column 54B adjacent to the outlet side cap 54D. A dialysate outlet port 54H is provided in a portion of the column 54B adjacent to the inlet side cap 54C. The dialysate is sent from the dialyzer 55 into the column 54B through the dialysate inlet port 54G. The dialysate and blood are exchanged via the hollow fiber membranes 54A, thereby purifying the blood. The dialysate after the exchange is returned to the dialyzer 55 via the dialysate outlet port 54H. The purified blood is sent to the venous side circuit 51 via the blood outlet port 54F.

In the venous side circuit 51, the purified blood is returned to the patient's body via a venous side puncture needle 56. The air trap chamber 10 is provided in the venous side circuit 51 in order to remove bubbles in the blood (debubble) when the blood is returned. For instance, a liquid (for example, blood or saline solution) flows into the air trap chamber 10 at a flow rate of 200 mL/min.

Figure 2:
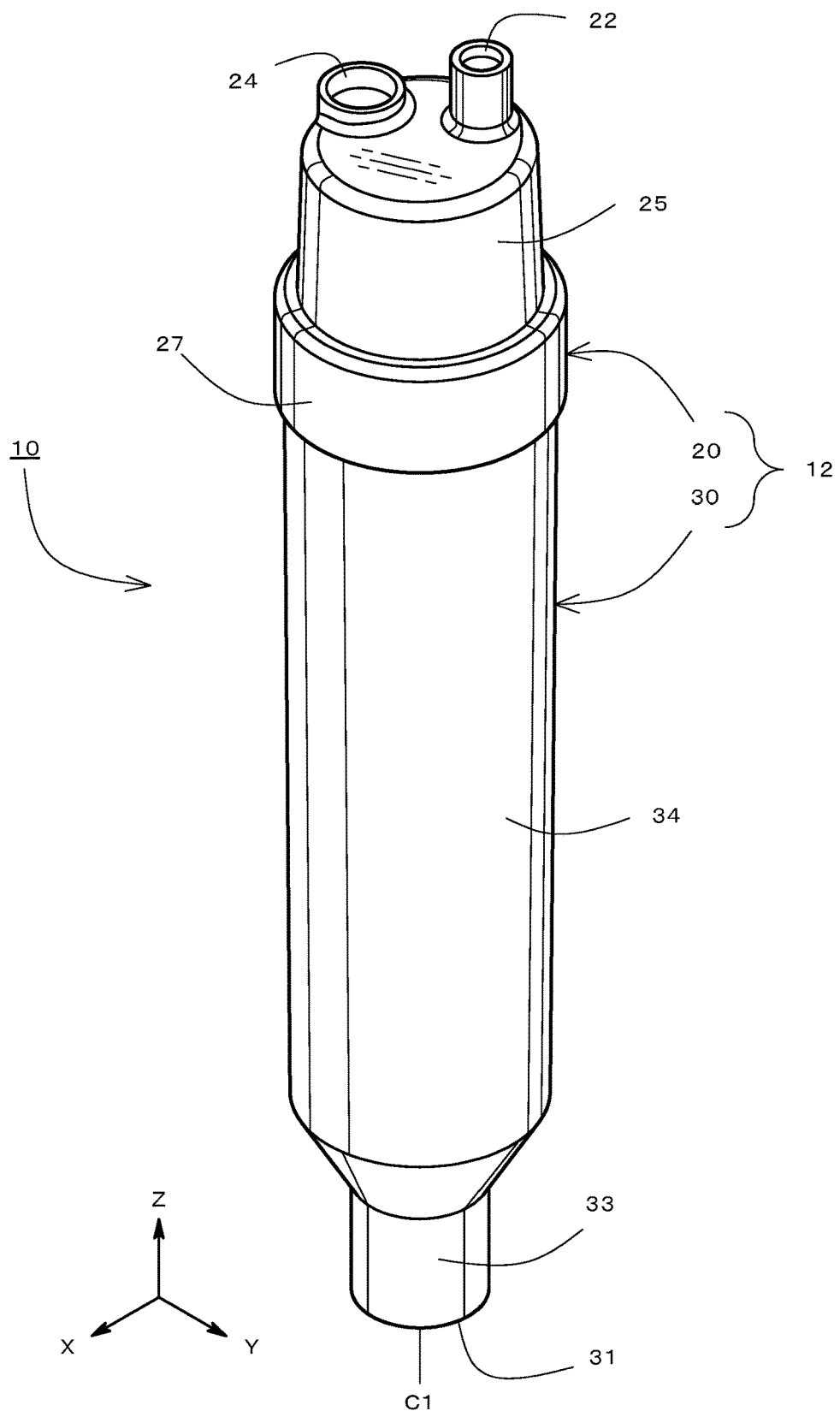
FIG. 2 is a perspective view illustrating the air trap chamber according to the embodiment.
Figure 3:
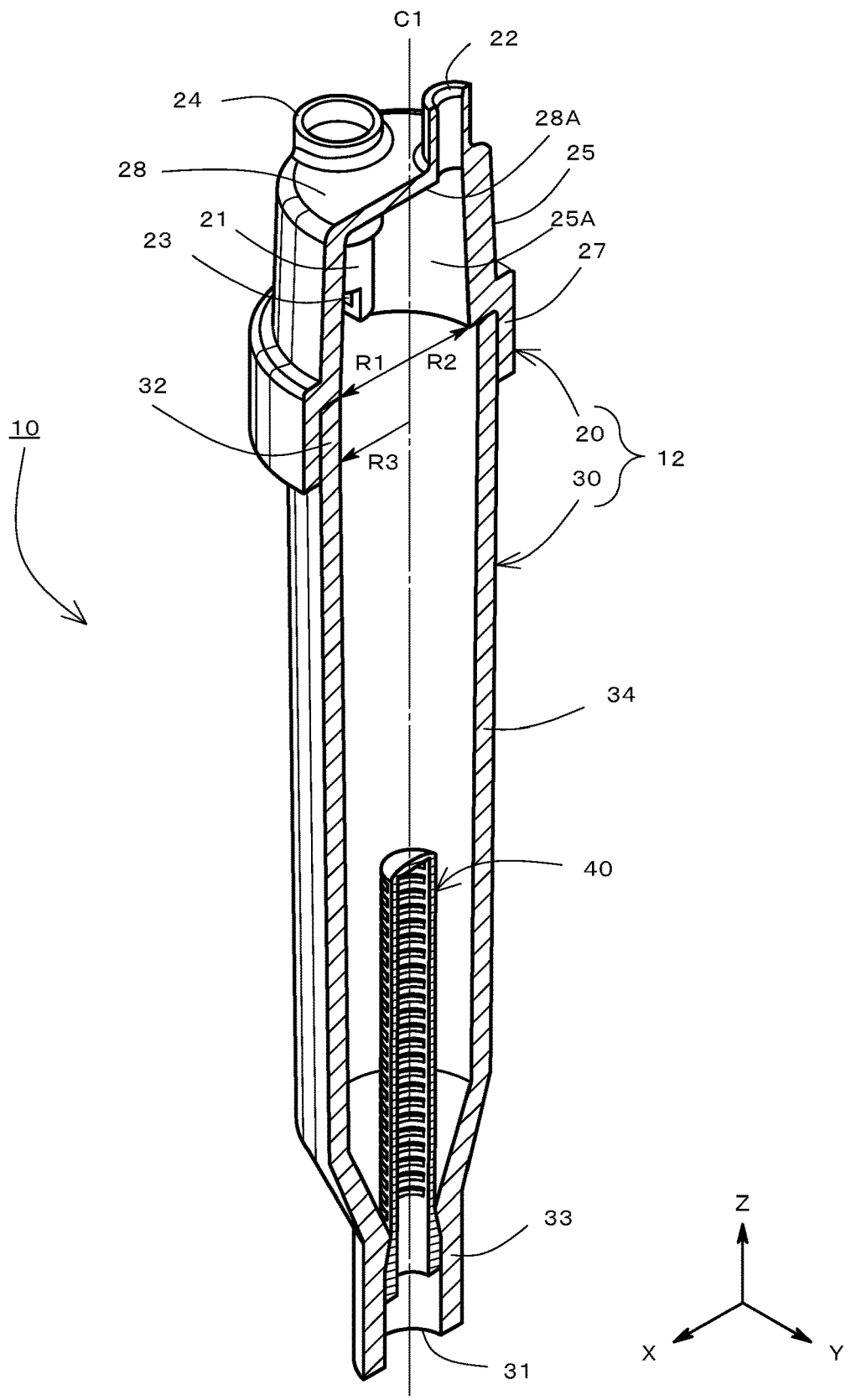
FIG. 3 is a perspective sectional view illustrating the air trap chamber according to the embodiment.

FIG. 2 illustrates the air trap chamber 10 according to the embodiment. FIG. 3 illustrates a perspective sectional view of the air trap chamber 10. The air trap chamber 10 includes a chamber body 12 and a filter 40.

During the dialysis treatment, the air trap chamber 10 is used upright so that its upper side in the drawing is the upper side and its lower side in the drawing is the lower side. Unless otherwise specified, the position and structure of each component will be described below with reference to the upright posture during use.

In addition, FIGS. 2 to 13 show an x-axis, a y-axis, and a z-axis orthogonal to each other. The Z-axis is a vertical axis extending along a central axis C1 of the air trap chamber 10. The X axis and the Y axis are two axes that are orthogonal to each other on a plane perpendicular to the Z axis. For example, the X axis is an axis perpendicular to a cut surface 23A (see FIG. 4) of an ejection port 23, and the Y axis is an axis parallel to the cut surface 23A.

The chamber body 12 has a substantially cylindrical shape, and its upstream end (upper end) with respect to the central axis C1 is covered with a top wall 28. The top wall 28 is provided with an inlet 24 and an air vent 22. An outlet 31 is provided at the downstream end (lower end) with respect to the central axis C1 of the chamber body 12. In other words, in the chamber body 12, a liquid (for example, blood or saline solution) flows down from the inlet 24 to the outlet 31.

The central axis C1 of the air trap chamber 10 may be determined depending on the shape of a housing 30, which occupies most of the chamber volume of the air trap chamber 10. For instance, the housing 30 has a cylindrical shape, or a frustoconical shape in which the diameter is slightly reduced toward the downstream side (as will be described later, these shapes are collectively referred to as a substantially cylindrical shape), and its central axis is the central axis C1 of the entire air trap chamber 10.

As described above, the chamber body 12 may include a cap 20 that is an upper member provided on the upstream side and the housing 30 that is a lower member provided on the downstream side. The cap 20 and the housing 30 are obtained by, for example, injection molding a resin.

The housing 30, having a substantially cylindrical shape, has a second connection flange 32 to be inserted into a first connection flange 27 of the cap 20, at the upstream end (upper end) with respect to the central axis C1. Note that the substantially cylindrical shape includes a shape in which the inner diameter is fixed with respect to the direction of the central axis C1, and also includes a shape, strictly speaking a conical shape, that has an inner diameter changing slightly (for example, 5% or less) with respect to the direction of the central axis C1 but is regarded as a substantially cylindrical shape because of such a slight increase in the inner diameter.

An outlet pipe 33 is formed at the downstream end (lower end) of the housing 30 with respect to the central axis C1. The lower end of the outlet pipe 33 is the outlet 31. The outlet 31 is coupled to a tube (not shown in the drawing) on the downstream side of the venous side circuit 51, and passes the liquid (for example, blood or saline solution) in the air trap chamber 10 to the venous side circuit 51.

The filter 40 is provided at the upper end of the outlet pipe 33. When a liquid (for example, blood or saline solution) is ejected from the air trap chamber 10, solid matters such as thrombus in the liquid are captured by the filter 40.

A housing body 34 is provided between the second connection flange 32 and the outlet pipe 33. The housing body 34 may have, for example, a substantially cylindrical shape; that is, a frustoconical shape whose diameter slightly decreases toward the outlet 31. The second connection flange 32 may have a cylindrical shape. In other words, the outer diameter of the second connection flange 32 to be in contact with the first connection flange 27 may be fixed with respect to the direction of the central axis C1.

Referring to FIG. 3, the inner diameter (inner circumference surface radius) R3 of the second connection flange 32 may be equal to the first radius R1 of the cap body 25. When the cap body 25 has a tapered cross-section that extends toward the downstream side; that is, a frustoconical shape, the first radius R1 at the lowermost end with the maximum diameter is equal to the inner diameter R3 of the second connection flange 32.

Figure 4:
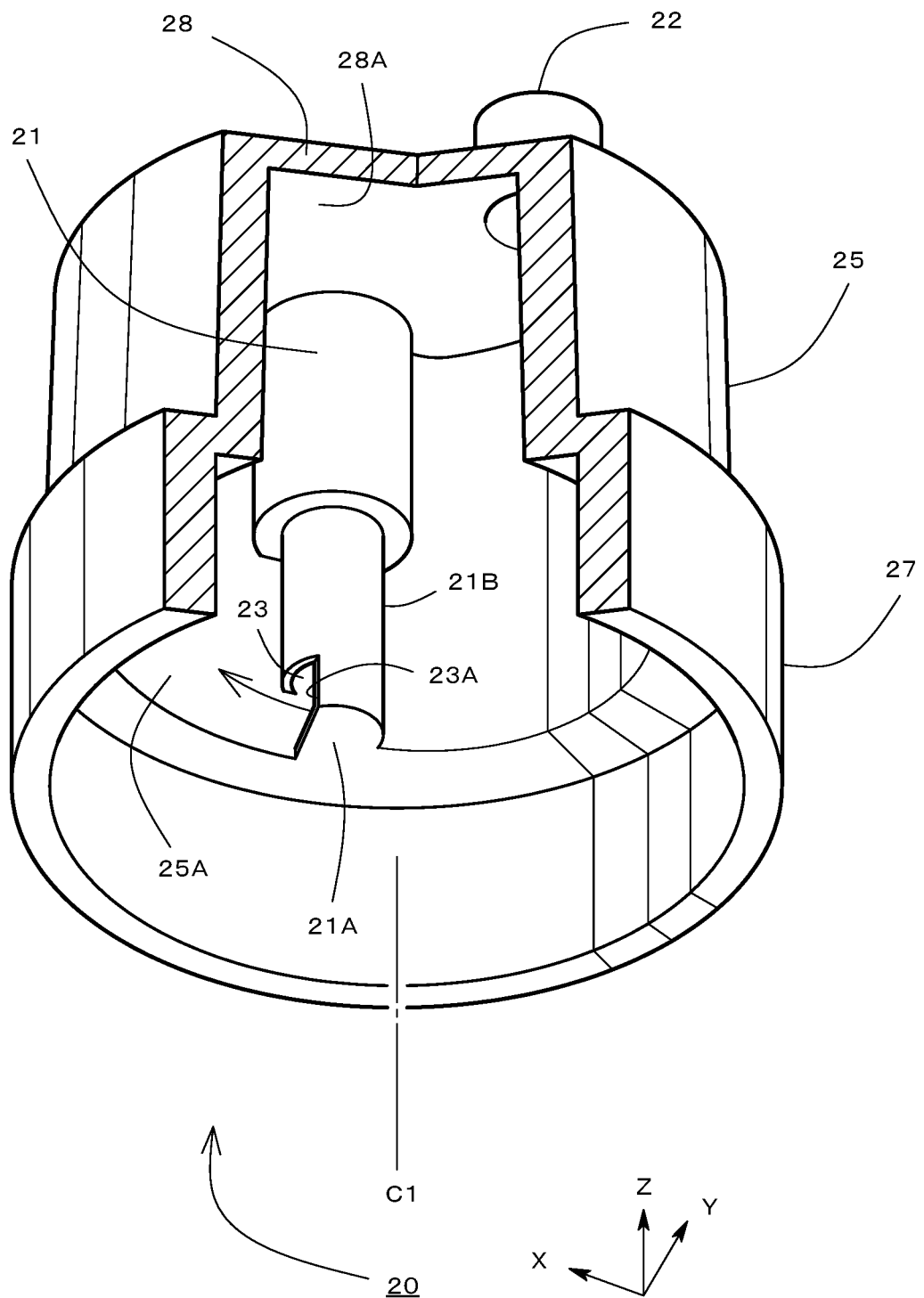
FIG. 4 is a diagram illustrating a structure of a cap of the air trap chamber according to the embodiment.

FIG. 4 illustrates a perspective sectional view of the cap 20 alone. In FIG. 4, the viewer looks up at the cap 20 obliquely from below. Additionally, in order to illustrate an inlet pipe 21, the cap body 25 and the first connection flange 27 are partially cut out in the circumferential direction.

The cap 20 is a member that has a U-shaped cross section and has the inlet 24 (see FIG. 3) and the air vent 22 at the upstream end (upper end). The cap 20 includes a top wall 28, a cap body 25, the first connection flange 27, and the inlet pipe 21.

The cap body 25 has a substantially cylindrical shape in which an upstream end (upper end) defined with respect to the central axis C1 of the chamber body 12; that is, a liquid contact portion whose inner surface is to come into contact with a liquid, is closed with the top wall 28. The inlet 24 (see FIG. 3) and the air vent 22 are formed in the top wall 28. The lower end of the cap body 25 is coupled to the first connection flange 27. The first connection flange 27 is the lower end of the cap 20 with respect to the direction of the central axis C1.

Figure 7:
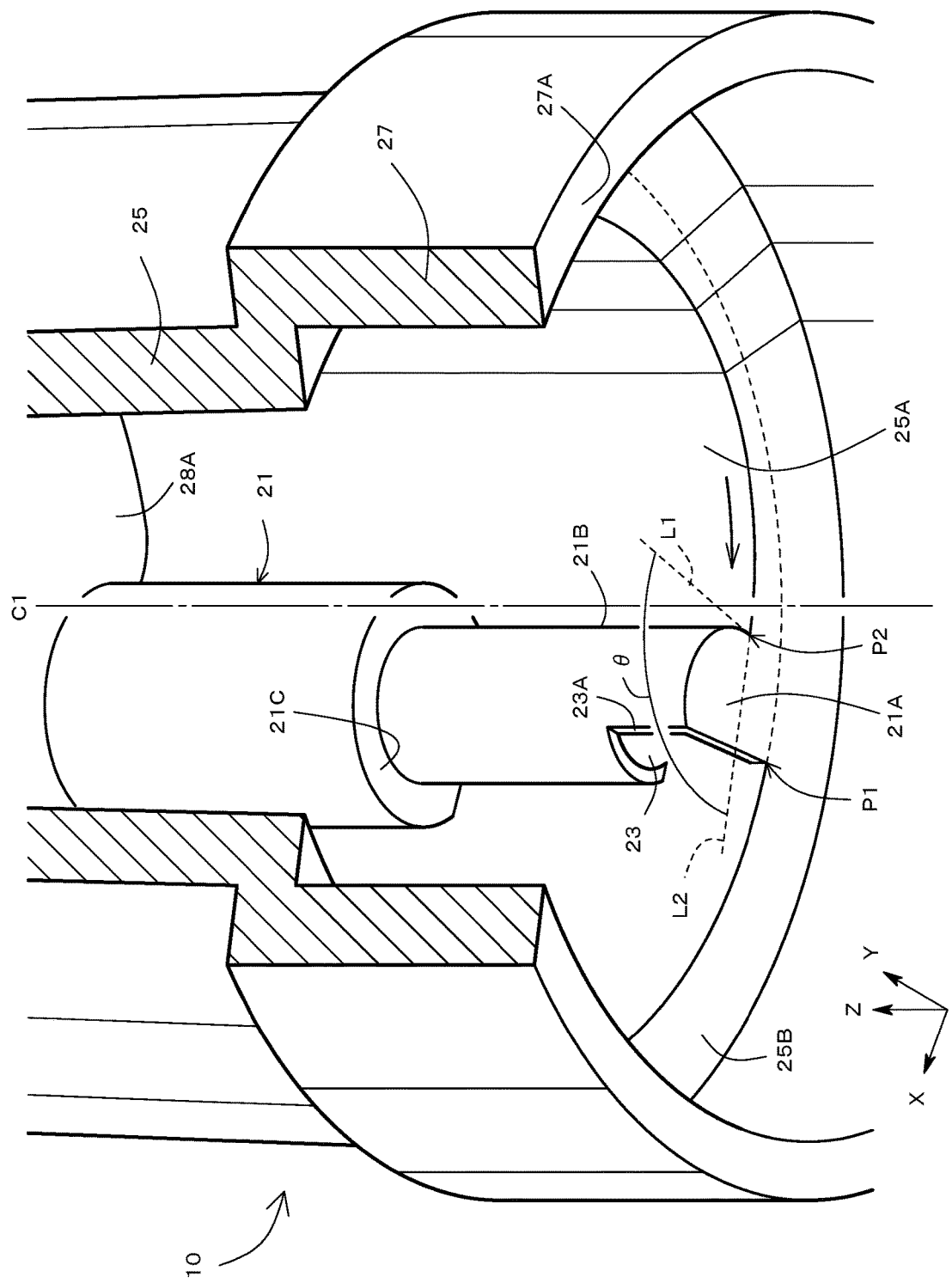
FIG. 7 is an enlarged view illustrating the structure of the cap of the air trap chamber according to the embodiment.

The first connection flange 27 is, for example, a cylindrical member extending along the central axis C1 and has an inner diameter made larger (increased) than the inner diameter of the cap body 25. Consequently, as illustrated in FIG. 7, the boundary between the cap body 25 and the first connection flange 27 has a step, and a lower end surface 25B (see FIG. 7) of the cap body 25 is exposed in the chamber.

Referring back to FIG. 4, the inlet pipe 21 is extended from the inlet 24 formed in the top wall 28 into the inside of the cap body 25; that is, the inside of the chamber body 12. When the air trap chamber 10 is provided in the venous side circuit 51, the inlet 24 at the upper end of the inlet pipe 21 is coupled to the tube on the upstream side of the venous side circuit 51. The ejection port 23, which is an end opening for ejecting the liquid into the chamber body 12, is formed at the lower end of the inlet pipe 21. As the ejection port 23 is provided below an inner surface 28A of the top wall 28 in this way, the gas retained on the inner surface 28A of the top wall 28 is prevented from entering the ejection port 23.

The ejection port 23 of the inlet pipe 21 is provided along an inner circumference surface 25A of the cap body 25, and has an opening faced in the circumferential direction of the inner circumference surface 25A. For instance, a lower wall 21A is formed at the lower end of the inlet pipe 21 and its side wall is cut out, forming the ejection port 23. For instance, the ejection port 23 is faced parallel to the tangential direction of the inner circumference surface 25A. The cut surface 23A of the ejection port 23 is formed so as to be parallel to the radial direction of the inner circumference surface 25A.

Since the ejection port 23 is provided at the inner circumference surface 25A of the cap body 25 and faced in the circumferential direction, the flow of the liquid (for example, blood or saline solution) flowing out from the ejection port 23 becomes a swirl flow along the inner circumference surface 25A. Since the liquid flow in the air trap chamber 10 becomes a swirl flow, the retention of the liquid in the air trap chamber 10 is suppressed as compared with the case where a specific flow is not formed.

Moreover, since the ejection port 23 is off the central axis C1 while the outlet 31 is provided on the axis of the central axis C1, the ejection port 23 and the outlet 31 are positioned off-axis with respect to each other. In other words, the ejection port 23 and the outlet 31 are separated from each other in the axial direction (X-axis direction and Y-axis direction) orthogonal to the central axis C1.

As the axes of the ejection port 23 and the outlet 31 are displaced in this manner, the entry of bubbles flowing back from the outlet 31 into the ejection port 23 is suppressed. In other words, in the event of a backflow in which bubbles enter the outlet 31 of the air trap chamber 10 from the downstream side of the venous side circuit 51, the bubbles rise due to buoyancy. At this time, since the ejection port 23 is off the axis of the opening of the outlet 31, the entry of the bubbles rising into the ejection port 23 is suppressed.

Figure 5:
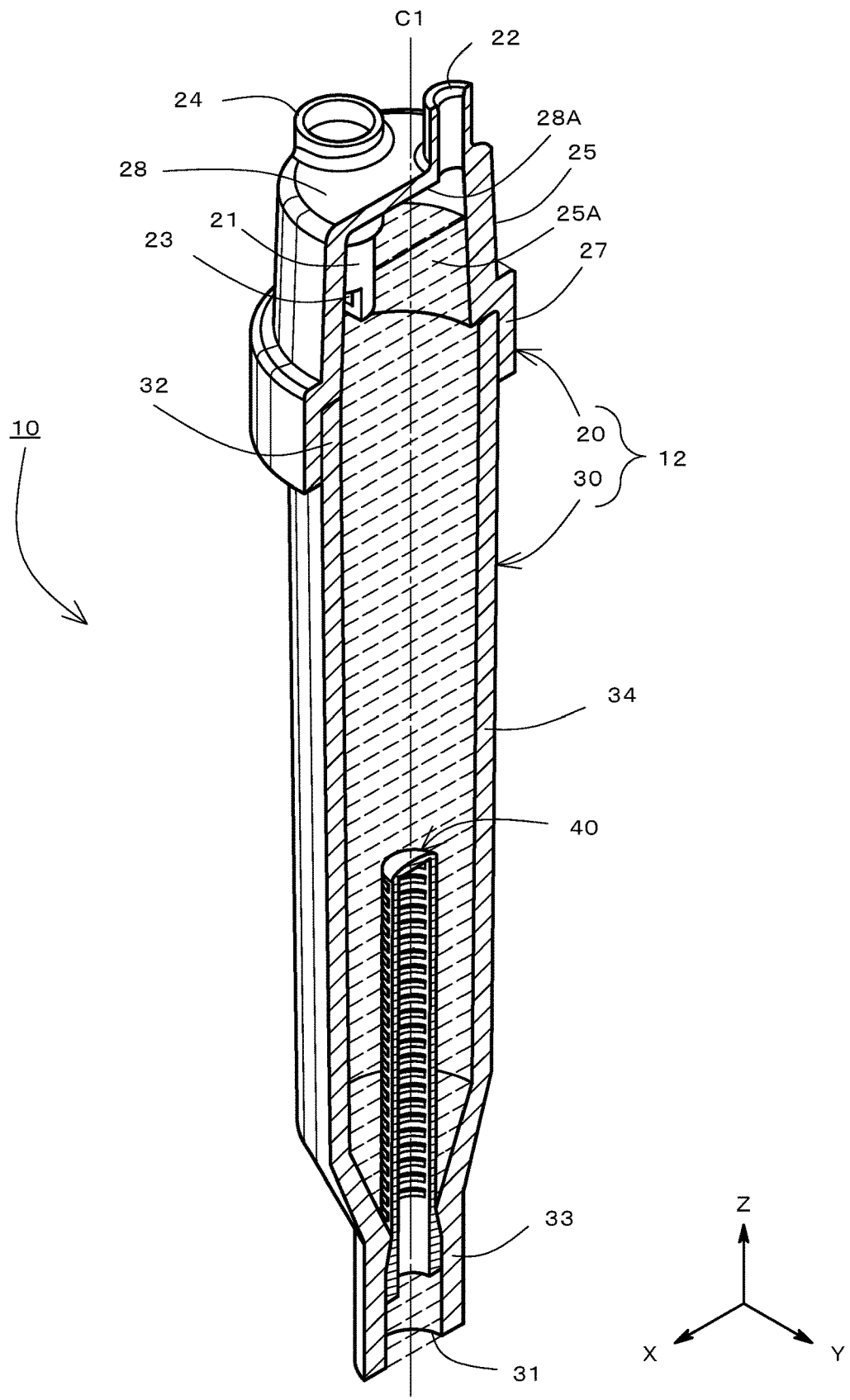
FIG. 5 is a perspective sectional view illustrating the air trap chamber according to the embodiment during use.

FIG. 5 shows an example of the use of the air trap chamber 10 according to the embodiment. The use includes that during priming and hemodialysis (treatment). The air trap chamber 10 according to the embodiment is a so-called airless chamber, and the liquid level is set near the inner surface 28A of the top wall 28 of the cap 20.

Figure 6:
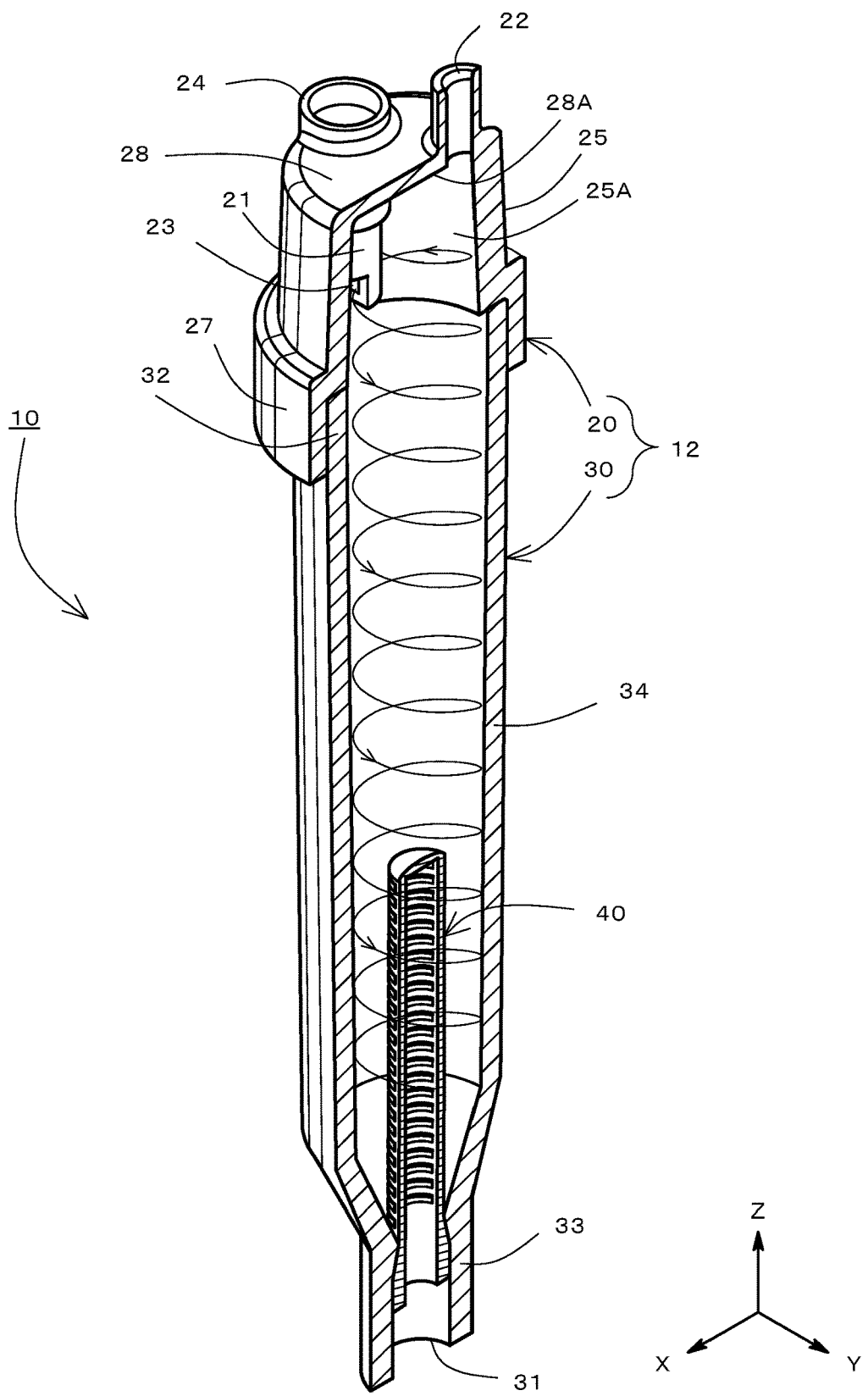
FIG. 6 is a diagram illustrating the flow in the air trap chamber according to the embodiment.

As the liquid level is set near the inner surface 28A of the top wall 28, the ejection port 23 below the inner surface 28A is submerged below the liquid surface. When the liquid is ejected from the ejection port 23 in this state, a swirl flow illustrated in FIG. 6 is generated along the inner circumference surface 25A of the cap body 25 as described above.

The swirl flow generated from the ejection port 23 flows downward while swirling and heads for the outlet 31. During this time, bubbles in the liquid rise due to buoyancy. The risen bubbles are removed from the air vent 22.

Following (being dragged by) the swirl flow generated from the ejection port 23, a swirl flow also occurs in the liquid above the ejection port 23. At this time, as illustrated in FIG. 7, the liquid flowing along the inner circumference surface 25A of the cap body 25 (that is, the chamber body 12) hits an outer circumferential surface 21B of the inlet pipe 21, and the flow may be stagnated.

Accordingly, in the air trap chamber 10 according to the embodiment, the inner circumference surface 25A of the cap body 25 is formed so as to extend in a spiral shape (a single spiral shape) in the circumferential direction from an ejection point P1 where the ejection port 23 is located to a connection point P2 where the outer circumferential surface 21B of the inlet pipe 21 that surrounds the ejection port 23 is coupled to the inner circumference surface 25A. At this time, a first distance (first straight line distance) connecting the ejection point P1 and the central axis C1 of the air trap chamber 10 on a plane (XY plane) perpendicular to the central axis C1 of the cap body 25 (i.e., the chamber body 12) is longer than a second distance (second straight line distance) connecting the connection point P2 and the central axis C1 on the same plane.

For example, when the inner circumference surface 25A is formed in a spiral shape, the radius is changed according to the angle to the central axis C1 as a rotation axis. Geometrically, the spiral shape includes an Archimedes' spiral represented by $r=a\theta$ in polar coordinates, and a logarithmic spiral represented by $r=ae^{b\theta}$ in polar coordinates. In this case, the second radius R2 connecting the connection point P2 and the central axis C1 is shorter than the first radius R1 connecting the ejection point P1 and the central axis C1 of the air trap chamber 10.

As the second radius R2 at the connection point P2 is made relatively small (the second distance is made relatively short), the flow rate of the liquid hitting the outer circumferential surface 21B of the inlet pipe 21 is reduced. As a result, the retention in the area is suppressed.

The phrase "the inner circumference surface 25A is formed in a spiral shape" does not necessarily mean that the inner circumference surface 25A is formed in the aforementioned geometric spiral rounded surface for the entire circumference. For instance, the rounded surface of the inner circumference surface 25A may be formed by connecting two types of arcs. In other words, a part of the inner circumference surface 25A including the ejection point P1 is formed based on an arc having the radius R1 centered at the central axis C1 as the origin. The other part of the inner circumference surface 25A is formed based on an arc with the radius R1 centered at an origin distanced from the ejection point P1 more than the central axis C1, and the intersection with the inlet pipe 21 is defined as the connection point P2. At this time, the first distance (first straight line distance) connecting the ejection point P1 and the central axis C1 on a plane perpendicular to the central axis C1 is longer than the second distance (second straight line distance) connecting the connection point P2 and the central axis C1 on the same plane. So-called R machining (round machining) is preferably performed on a connection point between an arc having the radius R1 centered at the central axis C1 as the origin and an arc having the radius R1 centered at an origin distanced from the ejection point P1 more than the central axis C1 so that the inner circumference surface 25A can be generally rounded for the entire circumference.

The effect of suppressing retention produced by the spiral shape of the inner circumference surface 25A of the cap body 25 according to this embodiment will be described with reference to FIGS. 8 to 11. The upper parts of FIGS. 8 to 11 show the cap 20 as viewed vertically from below. In other words, FIGS. 8 to 11 show the cap 20 as viewed from below the cap 20 along the central axis C1.

The lower parts of FIGS. 8 to 11 illustrate the results of fluid analysis in the inner circumference surface 25A of the cap body 25 in the respective shapes shown in the upper parts of FIGS. 8 to 11. In the analysis results, a region with a relatively high flow rate [m³/s] is hatched with a short pitch (short intervals), and a region with a relatively low flow rate is hatched with a long pitch. In particular, in the drawing, the region with the lowest flow rate is hatched with dashed lines.

Figure 8:
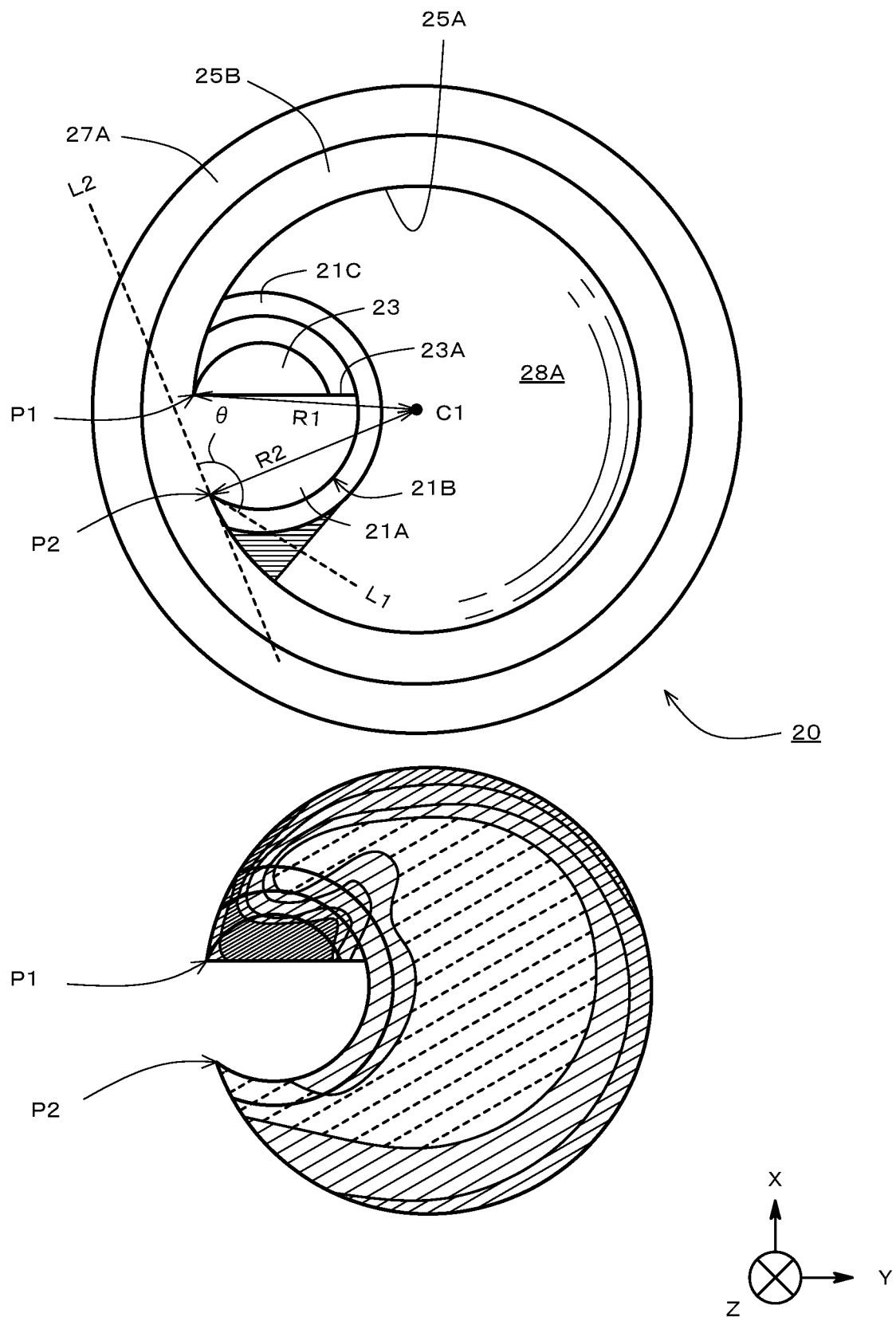
FIG. 8 is a diagram illustrating a structure of a cap (θ=150°) according to a comparative example and a fluid analysis result for the structure.

Referring to the upper part of FIG. 8, and FIG. 7, a lower end surface 27A of the first connection flange 27, the lower end surface 25B of the cap body 25, and the inner surface 28A of the top wall 28 are exposed on the radially outside when viewed from the angle in FIG. 8. The step surface 21C of the inlet pipe 21 and the lower wall 21A of the inlet pipe 21 are also exposed.

FIG. 8 illustrates a cap 20 as a comparative example. The inner circumference surface 25A of the cap 20 is a perfect circle, and the radius R1 from the central axis C1 at the ejection point P1 and the radius R2 from the central axis C1 at the connection point P2 are made equal (R1=R2).

In this case, a connection point angle θ, which is the angle that is formed between the tangent line L1 of the outer circumferential surface 21B of the inlet pipe 21 and the tangent line L2 of the inner circumference surface 25A of the cap body 25 at the connection point P2, and straddles the outer circumferential surface 21B of the inlet pipe 21 is an obtuse angle when, for example, the diameter of the inlet pipe 21 is smaller than the inner diameter (inner radius) of the cap body 25. At this time, at the connection point P2, the outer circumferential surface 21B of the inlet pipe 21 and the inner circumference surface 25A of the cap body 25 form a dead-end structure (indicated by hatching in the upper part of FIG. 8), so that the liquid flowing into the structure is retained.

Figure 9:
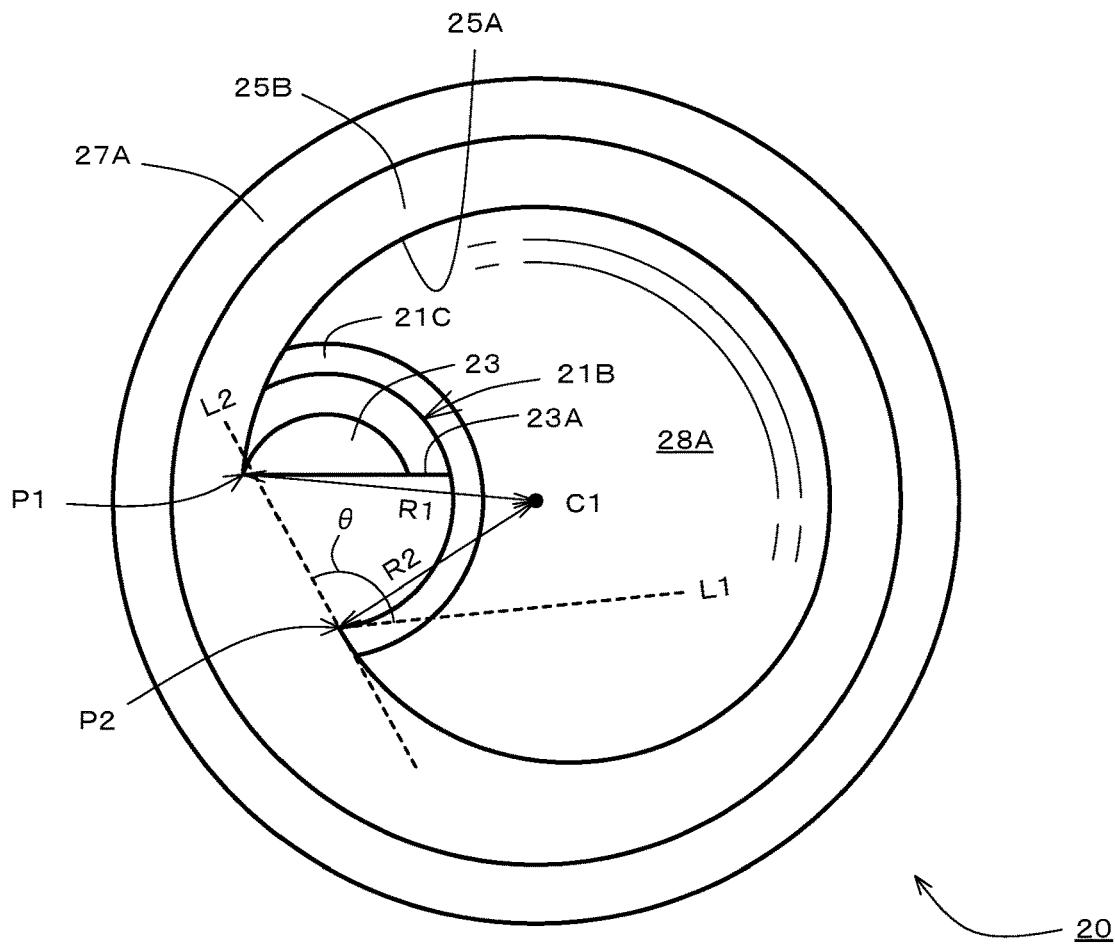
FIG. 9 is a diagram illustrating a structure of a cap (θ=120°) according to a first embodiment and a fluid analysis result for the structure.
Figure 9:
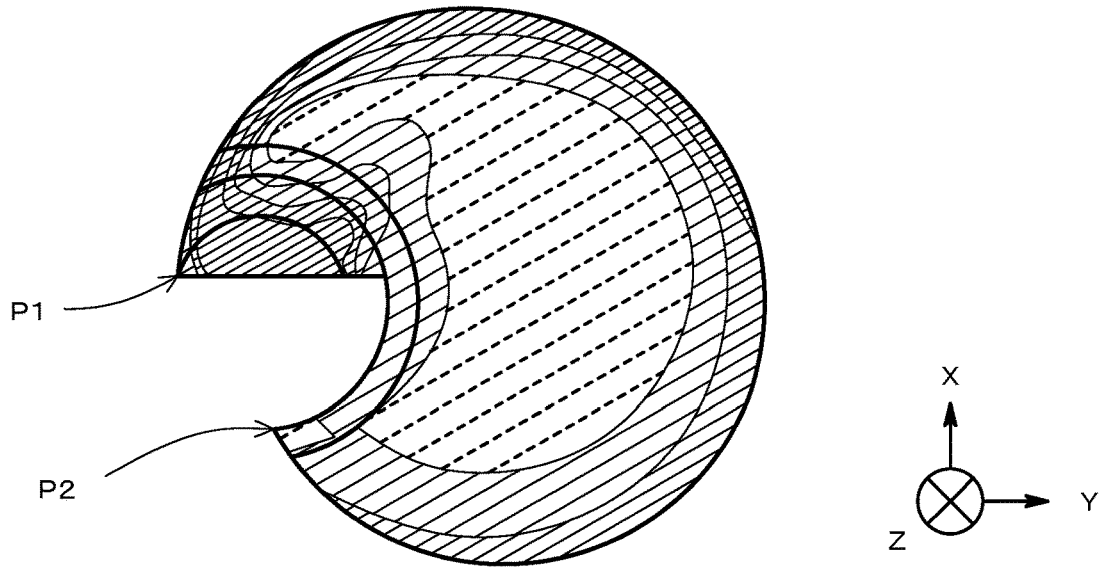

FIG. 9 illustrates the cap 20 according to this embodiment (first embodiment). The inner circumference surface 25A of this cap 20 has a spiral shape and is formed so that the radius R2 from the central axis C1 at the connection point P2 is shorter than the radius R1 from the central axis C1 at the ejection point P1.

Also in this case, a connection point angle θ, which is the angle that is formed between the tangent line L1 of the outer circumferential surface 21B of the inlet pipe 21 and the tangent line L2 of the inner circumference surface 25A of the cap body 25 at the connection point P2, and straddles the outer circumferential surface 21B of the inlet pipe 21 is an obtuse angle. However, since R2<R1, the flow rate of a liquid flowing into the connection point P2 is reduced in the first place, so that a comparison between the region (region indicated by dashed line hatching) with the minimum flow rate at the connection point P2 and the comparative example FIG. 8 shows that the retention is suppressed.

Figure 10:
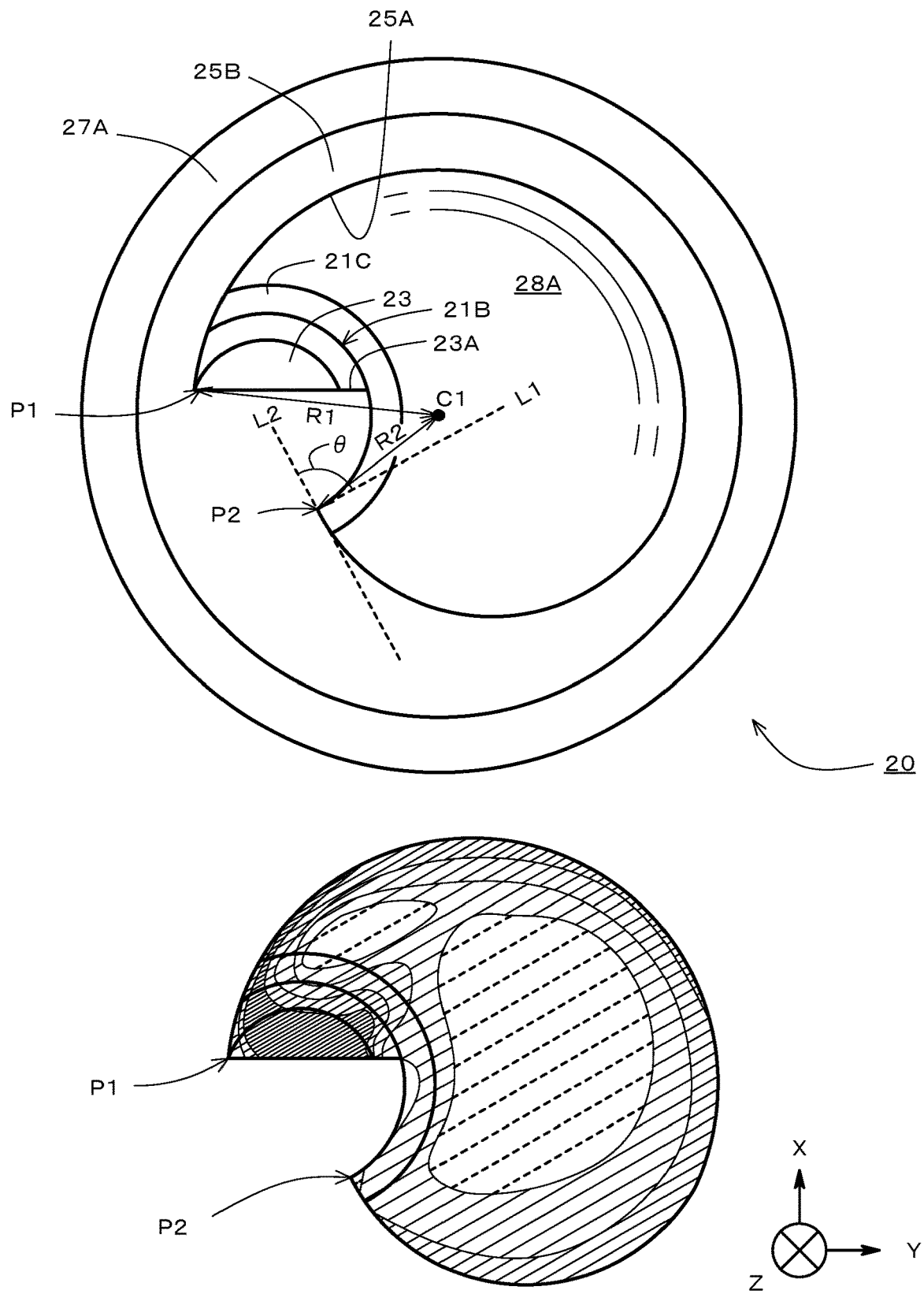
FIG. 10 is a diagram illustrating a structure of a cap (θ=90°) according to a second embodiment and a fluid analysis result for the structure.

FIG. 10 illustrates a cap 20 according to this embodiment (second embodiment). The inner circumference surface 25A of this cap 20 also has a spiral shape and is formed so that the radius R2 from the central axis C1 at the connection point P2 is shorter than the radius R1 from the central axis C1 at the ejection point P1.

In this case, a connection point angle θ, which is the angle that is formed between the tangent line L1 of the outer circumferential surface 21B of the inlet pipe 21 and the tangent line L2 of the inner circumference surface 25A of the cap body 25 at the connection point P2, and straddles the outer circumferential surface 21B of the inlet pipe 21 is a right angle (90°). Consequently, the dead-end structure consisting of the outer circumferential surface 21B of the inlet pipe 21 and the inner circumference surface 25A of the cap body 25 at the connection point P2 is eliminated. As a result, the retention is suppressed more than in the example shown in FIG. 9. It is preferable that the connection point angle θ to be 90° or less in order to eliminate this dead-end structure.

Figure 11:
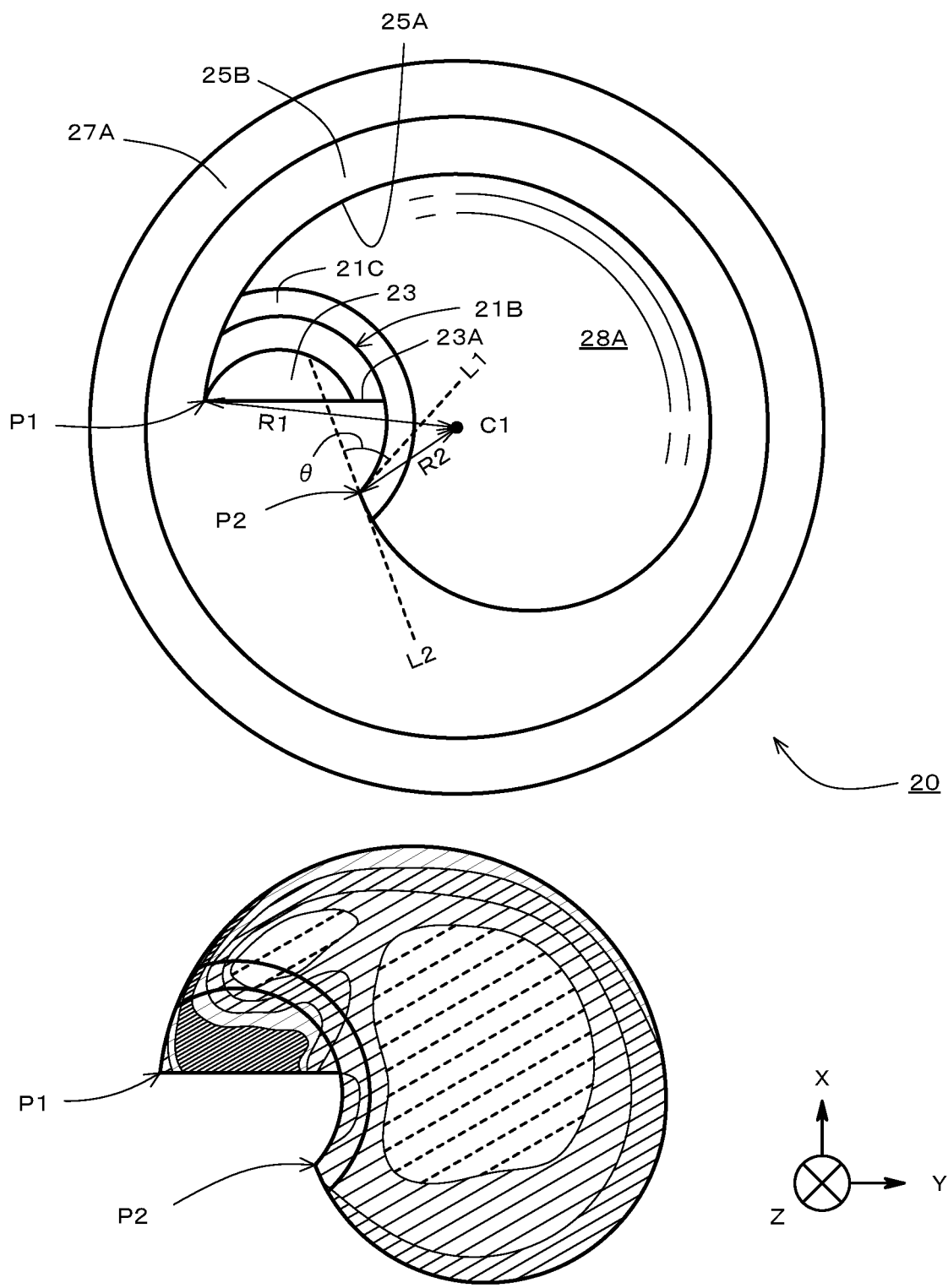
FIG. 11 is a diagram illustrating a structure of a cap (θ=60°) according to a third embodiment and a fluid analysis result for the structure.

FIG. 11 illustrates a cap 20 according to this embodiment (second embodiment). The inner circumference surface 25A of this cap 20 also has a spiral shape and is formed so that the radius R2 from the central axis C1 at the connection point P2 is shorter than the radius R1 from the central axis C1 at the ejection point P1.

In this case, a connection point angle θ, which is the angle that is formed between the tangent line L1 of the outer circumferential surface 21B of the inlet pipe 21 and the tangent line L2 of the inner circumference surface 25A of the cap body 25 at the connection point P2, and straddles the outer circumferential surface 21B of the inlet pipe 21 is an acute angle (60°). Hence, the angle between the outer circumferential surface 21B of the inlet pipe 21 and the inner circumference surface 25A of the cap body 25 at the connection point P2 is larger than in the example shown in FIG. 10, facilitating a flow into the central axis C1 side.

Thus, as shown in the fluid analysis results in FIGS. 8 to 11, the inner circumference surface 25A of the cap body 25 according to this embodiment has a spiral structure, so that the retention at the connection point P2 can be suppressed more than in the conventional example (FIG. 8).

Figure 12:
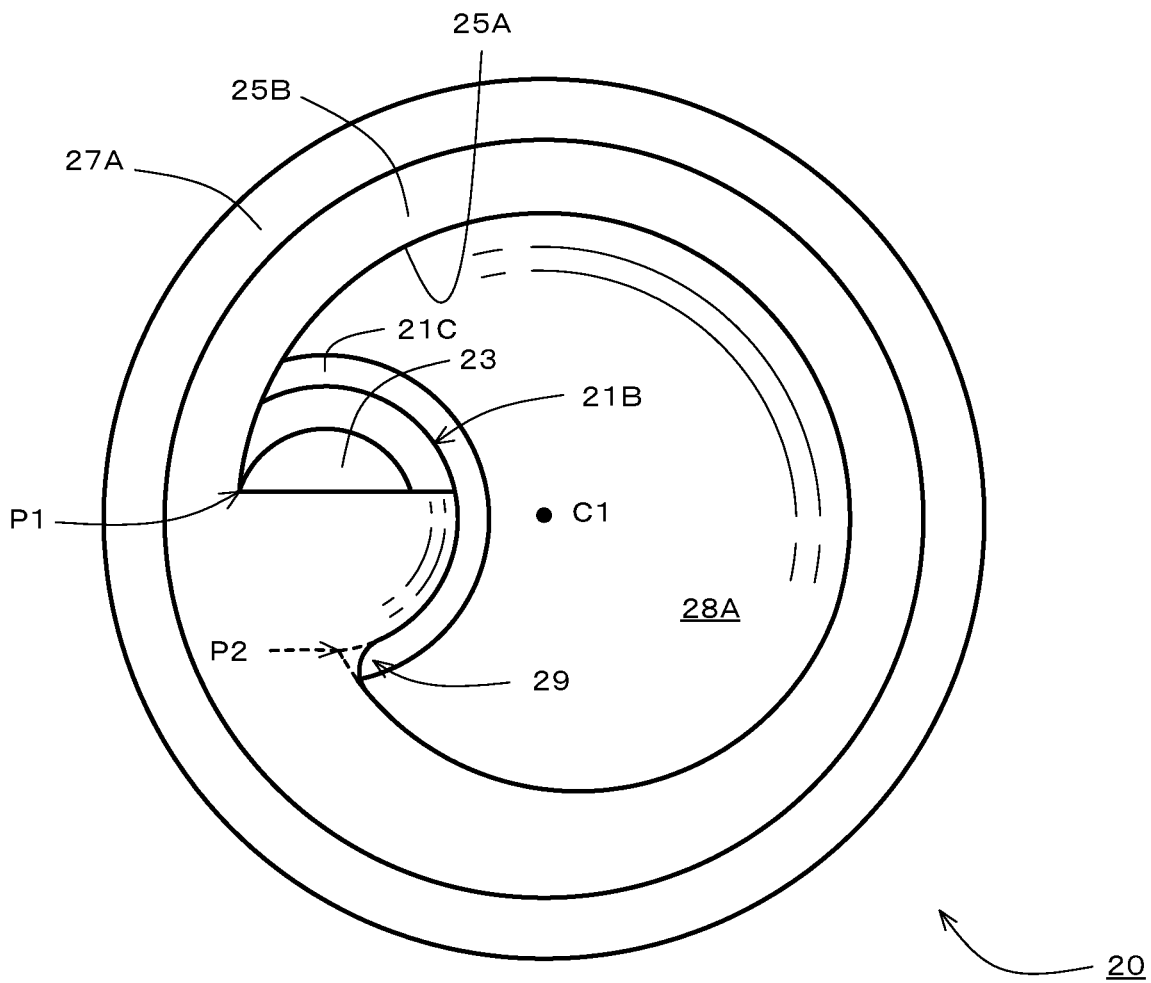
FIG. 12 is a diagram illustrating an R portion formed around the connection point of the cap.
Figure 12:
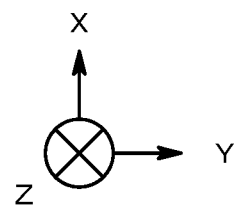

In order to more effectively suppress the retention at the connection point P2, an R portion 29 (rounded portion) may be formed around the connection point P2 as illustrated in FIG. 12. The R portion 29 has a round surface around an axis parallel to the central axis.

With the R portion 29 provided around the connection point P2 through which a liquid flows from the inner circumference surface 25A of the cap body 25 to the outer circumferential surface 21B of the inlet pipe 21, the liquid flows smoothly from the inner circumference surface 25A to the outer circumferential surface 21B.

Figure 13:
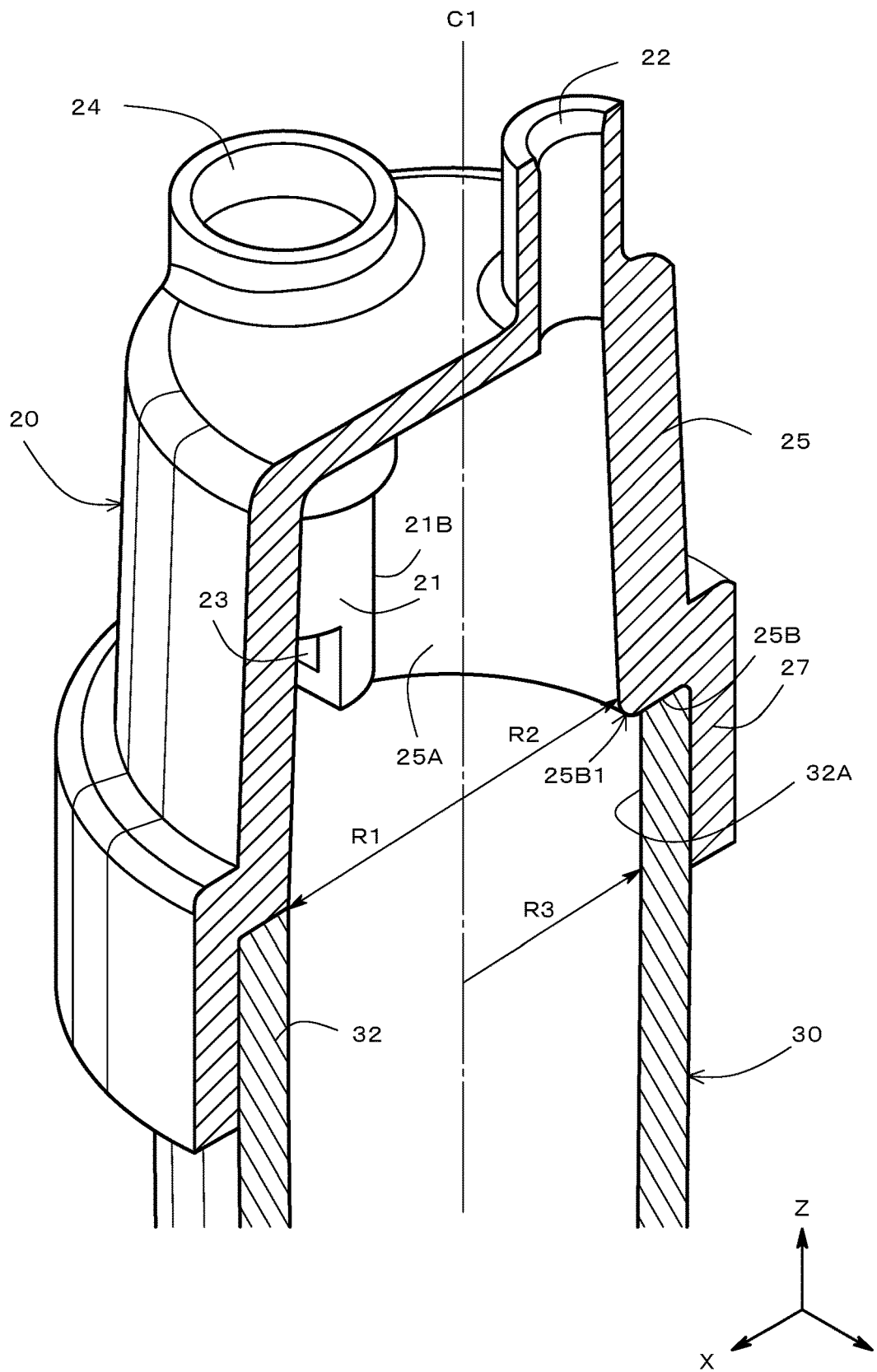
FIG. 13 is a diagram illustrating an R portion formed around a downstream end portion of the cap.
Figure 14:
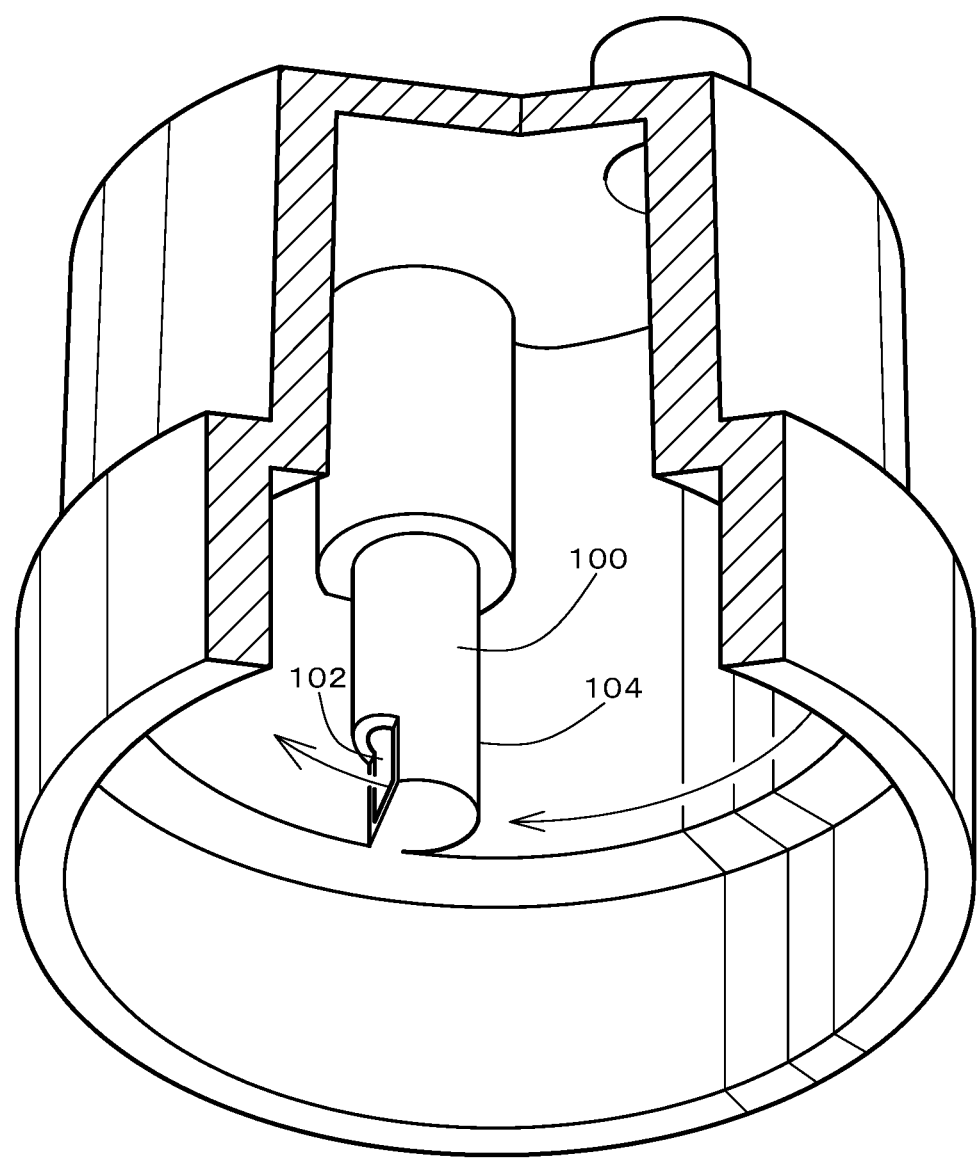
FIG. 14 is a diagram illustrating the structure of a cap of an air trap chamber according to a conventional technique.

Note that, as illustrated in FIG. 13, the inner diameter of the inner circumference surface 25A of the cap body 25 changes from R1 to R2, whereas the inner circumference surface 32A of the second connection flange 32 has a constant inner diameter R1 (=R3). Hence, the inner diameter R3 of the second connection flange is made larger than the second radius R2 of the inner circumference surface 25A of the cap body. Accordingly, a portion, having a radius R2, of the inner circumference surface 25A of the cap body 25 protrudes from the inner circumference surface 32A of the second connection flange 32, in the direction of the central axis C1.

Therefore, as illustrated in FIG. 13, an R portion 25B1 may be formed in a portion of at least the second radius R2 of the lower end surface 25B (downstream end) of the cap body 25. This allows the liquid to move smoothly from the cap body 25 to the second connection flange 32.

For example, the R portion 25B1 is formed by round machining, along a line extending in the circumferential direction of the inner circumference surface 25A, the angular structure formed by the lower end of the inner circumference surface 25A of the cap body 25 and the radially inner end of the lower end surface 25B.

Note that a chamfered portion may be provided instead of the R portion 25B1, so long as the liquid can smoothly move from the cap body 25 to the second connection flange 32.

REFERENCE SIGNS LIST

10 Air trap chamber, 12 Chamber body, 20 Cap, 21 Inlet pipe, 21B Outer circumferential surface of inlet pipe, 22 Air vent, 23 Ejection port, 24 Inlet, 25 Cap body, 25A Inner circumference surface of cap body, 25B Lower end surface of cap body, 25B1 R portion of lower end surface, 27 First connection flange, 28 Top wall, 28A Inner surface of top wall, 29 R portion around connection point, 30 Housing, 31 Outlet, 32 Second connection flange, 32A Inner circumference surface of second connection flange, 33 Outlet pipe, 34 Housing body, 50 Arterial side circuit, 51 Venous side circuit, 54 Blood purifier, 55 Dialyzer

The invention claimed is:

1. An air trap chamber comprising:
    a chamber body that has a substantially cylindrical shape and has an upstream end defined with respect to a central axis and covered with a top wall having an inlet, and a downstream end defined with respect to the central axis and having an outlet; and
    an inlet pipe that extends from the inlet into the chamber body, the inlet pipe including an ejection port, wherein
    the ejection port is an opening at an end of the inlet pipe and is provided at an inner circumference surface of the chamber body,
    the ejection port faces in a circumferential direction of the chamber body,
    the inner circumference surface of the chamber body extends, in a spiral shape in the circumferential direction, from an ejection point where the ejection port is located to a connection point where an outer circumferential surface of the inlet pipe surrounding the ejection port is coupled to the inner circumference surface of the chamber body, and a first distance connecting the ejection point and the central axis of the chamber body on a plane perpendicular to the central axis of the chamber body is longer than a second distance connecting the connection point and the central axis of the chamber body on the plane, and
    a connection point angle that is formed between a tangent line of the outer circumferential surface of the inlet pipe and a tangent line of the inner circumference surface of the chamber body at the connection point and straddles the outer circumferential surface of the inlet pipe is 90° or less.

2. The air trap chamber according to claim 1, wherein a round surface is formed at the connection point around an axis parallel to the central axis.

3. The air trap chamber according to claim 1, wherein
    the air trap chamber has a cap provided on an upstream side and a housing provided on a downstream side,
    the cap includes:
        a substantially cylindrical cap body,
        the inlet pipe in which the ejection port is provided at the inner circumference surface of the cap body and faced in the circumferential direction, and
        a first connection flange that is connected to the downstream end of the cap body and has a larger diameter than the cap body,
    the housing includes:
        a second connection flange to be inserted into the first connection flange, and
        a housing body coupled to the downstream side of the second connection flange,
    an inner diameter of the second connection flange of the housing is larger than the second distance of the inner circumference surface of the cap body, and
    a round surface or a chamfered portion is formed in at least a portion of the second distance of the downstream end of the cap body.

4. An extracorporeal circulation circuit that circulates removed blood and has a flow path to which the air trap chamber according to claim 1 is coupled.

* * * * *